United States Patent [19]

Chan

[11] 4,141,989

[45] Feb. 27, 1979

[54] FUNGICIDAL 3-(N-CHLOROACETYL-N-ARYLAMINO)-GAMMA-BUTYROLACTONE COMPOSITIONS

[75] Inventor: David C. K. Chan, Petaluma, Calif.

[73] Assignee: Chevron Research Company, San Francisco, Calif.

[21] Appl. No.: 837,121

[22] Filed: Sep. 29, 1977

Related U.S. Application Data

[63] Continuation-in-part of Ser. No. 731,491, Oct. 12, 1976, Pat. No. 4,107,323, which is a continuation-in-part of Ser. No. 631,351, Nov. 12, 1975, Pat. No. 4,012,519, which is a continuation-in-part of Ser. No. 548,660, Feb. 10, 1975, Pat. No. 3,933,860.

[51] Int. Cl.$^2$ .............................................. A01N 9/28
[52] U.S. Cl. .............................. 424/279; 424/DIG. 8
[58] Field of Search .......................... 424/279, DIG. 8

[56] References Cited

U.S. PATENT DOCUMENTS

| | | | |
|---|---|---|---|
| 3,741,989 | 6/1973 | Zaugg | 71/88 |
| 3,933,860 | 1/1976 | Chan | 424/274 |
| 4,012,519 | 3/1977 | Chan | 424/279 |

*Primary Examiner*—V. D. Turner
*Attorney, Agent, or Firm*—Dix A. Newell; T. G. DeJonghe

[57] ABSTRACT

Fungicidal compositions containing 3-(N-chloroacetyl-N-2,6-dimethylphenylamino)-gamma-butyrolactone or 3-(N-chloroacetyl-N-2,6-dimethylphenylamino)-5-methyl-gamma-butyrolactone, as the active ingredient, are highly effective for the prevention and eradication of downy mildew fungal diseases and *Phytophthora* crown and root rot diseases.

3 Claims, No Drawings

FUNGICIDAL 3-(N-CHLOROACETYL-N-ARYLAMINO)-GAMMA-BUTYROLACTONE COMPOSITIONS

RELATED APPLICATIONS

This application is a continuation-in-part of application Ser. No. 731,491, filed Oct. 12, 1976, now U.S. Pat. No. 4,107,323, which in turn is a continuation-in-part of application Ser. No. 631,351, filed Nov. 12, 1975, now U.S. Pat. No. 4,012,519, which in turn is a continuation-in-part of application Ser. No. 548,660, filed Feb. 10, 1975, now U.S. Pat. No. 3,933,860, the disclosures of which are incorporated herein by reference.

DESCRIPTION OF THE PRIOR ART

U.S. Pat. No. 3,933,860, issued to David Cheong King Chan on Jan. 27, 1976, and U.S. Pat. No. 4,012,519, issued to David Cheong King Chan on Mar. 15, 1977, disclose the use of a large class of 3-(N-acyl-N-arylamino) lactones and 3-(N-acyl-N-arylamino) lactams as protectant fungicides. These patents do not teach curative or eradicant fungicidal activity for any of the 3-(N-acyl-N-arylamino) lactones or lactams disclosed in the patents.

U.K. Pat. No. 1,445,387, published Aug. 11, 1976, and U.S. Pat. No. 4,015,648, issued May 24, 1977 to H. Moser, disclose the use of N-(methoxycarbonylethyl)-N-haloacetylanilines as preventive and curative fungicides. It has been found by comparative testing that a compound of the subject invention is substantially more effective as an eradicant or curative fungicide than the fungicides of these patents.

German Patent Publication Nos. 2,643,403 and 2,643,445, published Apr. 7, 1977, disclose the use of N-(alkylthiocarbonylethyl)acetanilides for controlling fungi, particularly those of the class *Phycomycetes*.

Netherlands Patent Publication No. 152,849, published Apr. 15, 1977, discloses the use of N-(alkoxymethyl)acetanilides as fungicides.

SUMMARY OF THE INVENTION

It has been found that fungicidal compositions containing 3-(N-chloroacetyl-N-2,6-dimethylphenylamino)-gamma-butyrolactone or 3-(N-chloroacetyl-N-2,6-dimethylphenylamino)-5-methyl-gamma-butyrolactones are effective for the control of downy mildew diseases and *Phytophthora* crown and root rot diseases. The compositions of the invention are effective both as protectant fungicides, i.e., they prevent or protect against fungal infections, and as eradicant fungicides, i.e., they eliminate and cure established infections. As described in more detail hereinbelow, the finding of eradicant activity for the fungicidal compositions of the present invention is highly advantageous. The compositions of the invention are especially preferred for the control of grape downy mildew because it has been found that they do not inhibit the fermentation of grapes harvested from grapevines treated with the compounds of the invention. Also, it has been discovered that the compositions of the present invention have surprisingly high effectiveness for eradicating grapevine downy mildew and that grapevine downy mildew fungi do not appear to develop resistance to the compositions.

DESCRIPTION OF THE INVENTION

The fungicidal compositions of the invention contain as the active ingredient a fungicidally effective amount of a compound represented by the formula

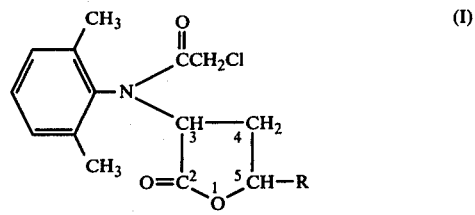

wherein R is hydrogen or methyl.

The compounds of formula (I) are described in U.S. Pat. No. 3,933,860.

The fungicidal compositions of the invention are highly effective for the control of plant downy mildew diseases caused by fungal species of the *Peronosporaceae* family and plant crown and root rots caused by soil-inhabiting fungal species of the *Phytophthora* genus.

Downy mildew is a widely distributed group of diseases of plants grown in the cool, humid areas of the world. Downy mildew diseases include downy mildew of lettuce caused by the speices *Bremia lactucae*; downy mildew of spinach caused by the species *Peronospora effusa*; downy mildew of onions caused by the species *P. destructor*; downy mildew of soybeans caused by the species *P. manshurica urica*; downy mildew of broccoli caused by the species *P. parasitica*; downy mildew of cabbage caused by the species *P. parasitica* ssp. *brassicae*; downy mildew of tobacco caused by the species *P. tabacina*; downy mildew of alfalfa caused by the species *P. trifoliorum*; downy mildew of sugar beets caused by the species *P. schactii*; downy mildew of lima beans caused by the species *Phytophthora phaseoli*; downy mildew of grapevines caused by the species *Plasmopara viticola*; downy mildew of watermelon, cucumber, squash and related plants caused by the species *Pseudoperonospora cubensis*; and downy mildew of hops caused by the species *Pseudoplasmopara humuli*.

Soil-inhabiting *Phytophthora* fungi cause a variety of crown and root rot diseases in plants. They are extremely difficult to control by fungicides because of the soil habitat of the fungus. Soil treatment to control the fungus is not generally effective, because many fungicides are not effectively distributed in soil and/or are detoxified in soil. Soil-inhabiting fungi can be controlled by downward systemic fungicides, i.e., a fungicide which translocates down to the roots of a plant after application of the fungicide to the plant foliage. However, most fungicides effective for the control of *Phytophthora* fungi do not possess downward systemic activity. The fungicides of the invention are systemic upward from the roots to the foliage and downward from the foliage to the roots. The fungicides of the invention are also not detoxified by the soil and are rapidly taken up by the roots of plants. Therefore, the fungicides of the invention are highly effective for the control of soil-inhabiting *Phytophthora* fungi.

*Phytophthora* species causing crown and root rot diseases in plants include *Phytophthora cactorum* (crown rot of walnut, root rot of sweetcloves, root cankers of avocado trees, *Phytophthora* rot of apples and pears); *P. cambivora* (ink disease of citrus trees); *P. capsici* (root rot of peppers); *P. cinnamoni* (heart and root rot of pineapples, *Phytophthora* root rot of avocadoes, root rot of citrus trees); *P. citricola* (brown rot gummosis); *P. citrophthora* (root rot of citrus trees); *P. cryptogea* (crown and root rot of tomato, safflower and tobacco); *P. dreschleri* (root rot of safflower); *P. erythrosytica* (pink rot of potato); *P. fragariae* (red stele of strawberry); *P. megosperma* (root rots of cherry, peach and walnuts); *P. nicotianae* (tobacco black shank); *P. palmivora* (root rot of citrus trees, bud rot of coconut palm, black pod rot of cacao); *P. parasitica* (root rot of watermelons, root rot of citrus trees); and *P. syringae* (root rot of citrus).

The fungicidal compositions of the invention are particularly useful fungicides because they cure established fungal infections. This permits economical use of the fungicides of the invention, because they need not be applied to plants unless fungal infection actually occurs. Thus, a preventive program of applying fungicides against potential fungal infection is not necessary.

Protectant or preventive fungicides and eradicant fungicides generally operate by completely different modes of action. For example, protectant or preventive fungicides generally prevent fungal infection by preventing sporulation and/or infection, whereas eradicant fungicides cure fungal diseases after the host is already infected. Therefore, it is highly surprising that the fungicides of the present invention act as both protectant and eradicant fungicides.

The compositions of the invention are applied in fungicidally effective amounts to fungi and/or their habitats, such as vegetative plant hosts and their growth medium or environment. The amount used will, of course, depend on several factors such as the host, the species of fungus and the particular composition of the invention. The fungicidal compositions of the invention generally contain conventional, biologically inert extenders or carriers normally employed for facilitating dispersion of the active fungicidal ingredient, recognizing that the formulation and mode of application may affect the activity of the fungicide. Thus, the fungicidal composition of the invention may be granules, powdery dusts, wettable powders, emulsifiable concentrates, solutions, or any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, for example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other non-volatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the active fungicide may vary according to the manner in which the composition is to be applied and the particular type of formulation, but in general comprise 0.5 to 95% of the active fungicide by weight of the fungicidal composition.

The fungicidal compositions may be formulated and applied with other active ingredients, including other fungicides, insecticides, nematocides, bactericides, plant growth regulators, fertilizers, etc.

EXAMPLES

The preparation, formulation and use of the fungicidal compositions of the invention are illustrated by the following examples.

EXAMPLE 1 — PREPARATION OF 3-(N-CHLOROACETYL-N-2,6-DIMETHYL-PHENYLAMINO)-GAMMA-BUTYROLACTONE (COMPOUND A)

A solution of 410 g (2 mols) N-2,6-dimethylphenylamino-gamma-butyrolactone, m.p. 85–86.5° C. and 197.5 g (2.5 mols) pyridine in 2 liters benzene was heated to reflux. To the solution was added dropwise 260 g (2.3 mols) chloroacetyl chloride over a 40-minute period. The reaction mixture was heated under reflux for 20 additional minutes, cooled and filtered to remove a precipitate of pyridine hydrochloride. The filtrate was washed with water, dried over magnesium sulfate and evaporated under reduced pressure to give a colorless white solid. The solid was slurried with isopropanol, filtered, and dried to give 501 g of product, as a colorless solid, m.p. 145.5°–147° C.

The product has an oral $LD_{50}$ (rats) of $>1000$ mg/kg and dermal $LD_{50}$ (rats) of $>2000$ mg/kg.

EXAMPLE 2 — PREPARATION OF 3-(N-CHLOROACETYL-N-2,6-DIMETHYL-PHENYLAMINO)-5-METHYL-GAMMA-BUTYROLACTONE (COMPOUND B)

A 500-ml round-bottom flask equipped with a two-way stopcock was charged with 24.2 g (0.2 mol) 2,6-dimethylaniline and 19.0 g (0.106 mol) alpha-bromo-gamma-valerolactone. The flask was evacuated to 20 mm of Hg, then slowly heated to 100° C. while periodically evacuating the flask by means of a water-aspirator to maintain the pressure at about 17–40 mm of Hg. After heating the reaction mixture at about 100° C. and at 17–40 mm of Hg for 22 hours, the reaction mixture was cooled and diluted with 300 ml ethyl ether. A solid precipitate of 2,6-dimethylaniline hydrobromide salt was removed by filtration. The filtrate was washed with 5% aqueous hydrochloric acid solution, water, dried over magnesium sulfate and evaporated under reduced pressure to give 19.2 g of 3-(N-2,6-dimethylphenylamino)-5-methyl-gamma-butyrolactone, as a viscous oil.

A 10.9-g (0.096-mol) sample of chloroacetyl chloride was added slowly to a solution of 19.2 g (0.088 mol) 3-(N-2,6-dimethylphenylamino)-5-methyl-gamma-butyrolactone and 7.6 g (0.096 mol) pyridine in 250 ml ethyl acetate. An exotherm ensued and a precipitate separated. After stirring for 16 hours at about 20° C, the reaction mixture was washed with water, washed with saturated aqueous sodium bicarbonate solution, washed with water, dried over magnesium sulfate and evaporated under reduced pressure to give a thick oil which crystallized from ethyl ether to give a yellow solid. The yellow solid was washed with cold ethyl ether/petroleum ether and air-dried to give 15.8 g of 3-(N-chloroacetyl-N-2,6-dimethylphenylamino)-5-methyl-gamma-butyrolactone, m.p. 128°–131° C.

EXAMPLE 3 — WETTABLE POWDER FORMULATION

A 50% wt. wettable powder formulations was prepared by mixing 52.1 parts by weight of 3-(N-chloroacetyl-N-2,6-dimethylphenylamino)-gamma-butyrolactone (96% purity), 42.9 parts by weight of attapulgite clay and 5 parts by weight of a blend of anionic surfactants, lignosulfonates and sodium stearate.

EXAMPLE 4 — AQUEOUS FLOWABLE FORMULATION

A 0.41 kg/liter flowable formulation was prepared by mixing 44.22 parts by weight of 3-(N-chloroacetyl-N-2,6-dimethylphenylamino)-gamma-butyrolactone (96% purity), 43.43 parts by weight water, 1.42 parts by weight of a polyvinyl acetate/polyvinyl alcohol antifoaming agent, 9.73 parts by weight of propylene glycol, 0.20 parts by weight of a polysaccharide thickener and 1 part by weight of a nonionic surfactant.

EXAMPLE 5 — PREVENTIVE GRAPE DOWNY MILDEW CONTROL

Compounds A and B, and several structurally related compounds, were tested for the control of the grape downy mildew organism *Plasmopara viticola*. Detached leaves, between 70 and 85 mm in diameter, of 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environment chamber and incubated at 18°–22° C. and about 100% relative humidity. Seven to nine days after inoculation, the amount of disease control was determined. The percent disease control provided by a given test compound was based on the percent disease reduction relative to untreated check plants. The test compounds, test concentrations and results are tabulated in Table I.

EXAMPLE 6 — ERADICANT GRAPE DOWNY MILDEW CONTROL

Compounds A and B and several structurally related compounds were tested for the eradicant control of the grape downy mildew organism *Plasmopara viticola*. Detached leaves of between 70 and 85-mm diameter of 7-week-old *Vitis vinifera* cultivar Emperor grape seedlings were used as hosts. The leaves were inoculated with the organism and placed in an environment chamber and incubated at 18°–22° C. and at about 100% relative humidity for 2 days. The leaves were then sprayed with a solution of the test compound in acetone. The sprayed leaves were then maintained at 18°–22° C. and at about 100% relative humidity. Seven to nine days ater inoculation, the amount of disease control was determined. The percent disease control provided by a given test compound was based on the percent disease reduction relative to nontreated check plants. The test compounds, the test concentrations and the results are tabulated in Table I.

TABLE I

Grape Downy Mildew Control with Compounds of the Formula

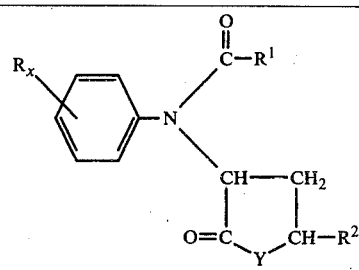

| | | | | | Grape Downy Mildew Control | | | | |
| | | | | | Preventive | | | Eradicative | | |
| No. | $R_x$ | $R^1$ | $R^2$ | Y | % | (ppm) | $ED_{50/90}$* | % | (ppm) | $ED_{50/90}$ |
| A | 2,6-$(CH_3)_2$ | $CH_2Cl$ | H | O | 97 | (6.4) | 1.2/4.4 | 99 | (6.4) | 1/3 |
| | | | | | 99 | (100) | | | | |

TABLE I-continued

Grape Downy Mildew Control with Compounds of the Formula

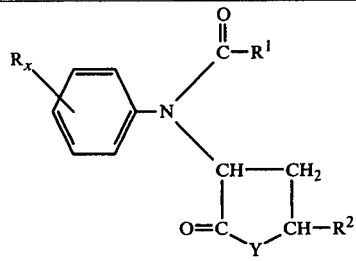

| | | | | | Grape Downy Mildew Control | | | | | |
|---|---|---|---|---|---|---|---|---|---|---|
| | | | | | Preventive | | | Eradicative | | |
| No. | $R_x$ | $R^1$ | $R^2$ | Y | % | (ppm) | $ED_{50/90}$* | % | (ppm) | $ED_{50/90}$ |
| B | 2,6-$(CH_3)_2$ | $CH_2Cl$ | $CH_3$ | O | 80 | (100) | 8/100 | 95 | ( 40) | 7/28 |
| 1 | 3,4-$Cl_2$ | $CH_2CH_3$ | H | O | 0 | (100) | — | 5 | ( 40) | — |
| 2 | 2,6-$(CH_3)_2$ | 3,4-$Cl_2$-$\phi$ | H | O | — | — | — | 29 | (100) | — |
| 3 | 2-$CH_3O$ | $CH_2Cl$ | H | O | 0 | (100) | — | 12 | (100) | — |
| 4 | 2,6-$(CH_3)_2$ | $CH_2Cl$ | H | $NCH_3$ | — | — | — | 3 | (100) | — |
| 5 | H | $CH_2Cl$ | H | O | — | — | — | 0 | (100) | — |
| 6 | 2,6-$(C_2H_5)_2$ | $CH_2Cl$ | H | O | 0 | (100) | — | 39 | (100) | — |
| 7 | 2-$iC_3H_7$ | $CH_2Cl$ | H | O | 3 | (100) | — | 17 | ( 16) | — |
| 8 | 2-$C_2H_5$ | $CH_2Cl$ | H | O | 0 | (100) | — | 0 | (100) | — |
| | | | | | | | | 95 | (100) | |
| 9 | 2,6-$Cl_2$ | $CH_2Cl$ | H | O | 0 | (100) | — | 67 | ( 40) | 35/70 |
| 10 | 3,4-$Cl_2$ | $CH_2Cl$ | H | O | 89 | (100) | 66/107 | 39 | (100) | — |
| 11 | 3,5-$Cl_2$ | $CH_2Cl$ | H | O | 45 | (100) | — | 54 | (100) | — |
| 12 | 2,6-$(C_2H_5)_2$ | $CH_2Cl$ | $CH_3$ | O | — | — | — | 87 | (100) | 38/100 |
| 13 | 2-$CH_3$-6-$C_2H_5$ | $CH_2Cl$ | H | O | 0 | (100) | — | 87 | (100) | — |
| 14 | 2-$CH_3$-6-$C_2H_5$ | $CH_2Cl$ | $CH_3$ | O | — | — | — | 29 | (100) | — |
| 15 | 2,6-$(CH_3)_2$ | $CH_2Br$ | H | O | — | — | — | 54 | (100) | 84/— |
| 16 | 2,6-$(CH_3O)_2$ | $Ch_2Cl$ | H | O | — | — | — | 67 | (100) | — |
| 17 | 2,6-$(CH_3)_2$ | $CH_2CH_2Cl$ | H | O | — | — | — | 50 | (100) | 117/— |
| 18 | 2,6-$(CH_3)_2$ | $CH_2Cl$ | H | $NCH(CH_3)_2$ | 15 | (100) | — | 37 | (100) | — |
| 19 | 2,6-$(CH_3)_2$ | $CCl=CCl_2$ | H | O | — | — | — | 15 | (100) | — |
| 20 | 2,6-$(CH_3)_2$ | $CH_2Cl$ | H | $NCH_2CH=CH_2$ | — | — | — | 0 | (100) | — |
| 21 | 2,6-$(CH_3)_2$ | $CH_2Cl$ | H | NH | — | — | — | 0 | (100) | — |
| 22 | 2,6-$(CH_3)_2$ | $CH_2Cl$ | H | N(3-$CH_3$-4-Cl)$\phi$ | — | — | — | 32 | (100) | — |
| 23 | 2,6-$(CH_3)_2$ | 4-Cl-$\phi$ | H | $NCH_3$ | — | — | — | 0 | (100) | — |
| 24 | 2,4,6-$(CH_3)_3$ | $CH_2Cl$ | H | O | — | — | — | 0 | (100) | — |
| 25 | 2-$CH_3$-6-t-$C_4H_9$ | $CH_2Cl$ | H | O | — | — | — | 0 | (100) | — |
| 26 | 3,4-$(CH_3)_2$ | $CH_2Cl$ | H | O | 12 | (100) | — | 87 | (100) | — |
| 27 | Open-chain ester** | | | | 78 | (100) | 32/152 | 96 | (100) | 5/10 |
| 28 | Captafol*** | | | | 84 | ( 40) | 22/54 | 74 | (200) | 100/310 |
| 29 | Bordeaux Mixture (water used as solvent) | | | | 100 | ( 40) | 2/13 | 100 | ( 40) | 5/19 |
| | | | | | 92 | ( 16) | | 86 | ( 16) | |

*$ED_{50}$ (ppm of applied spray for 50% control)
$ED_{90}$ (ppm of applied spray for 90% control)
$\phi$ = phenyl

EXAMPLE 7 — PREVENTIVE GRAPE DOWNY MILDEW CONTROL

A test was conducted to compare the effectiveness of 3-(N-chloroacetyl-N-2,6-dimethylphenylamino)-gamma-butyrolactone and two commercial fungicides for the control of grape downy mildew (*Plasmopara viticola*). The commercial fungicides used were Folpet [N-(trichloromethylthio)phthalimide] and Captafol [cis-N-(1,1,2,2-tetrachloroethylthio)-4-cyclohexene-1,2-dicarboximide]. The test was conducted as follows:

Detached leaves of 3-month-old Cabernet Sauvignon grape plants were used as hosts. Four leaves were used in each test. The leaves were sprayed with a solution of the test compound in a 1% acetone/99% water solution containing 40 ppm of a nonionic surfactant. The sprayed leaves were dried and inoculated with 25 droplets of a sporangial suspension of the organism (400,000 conidia/milliliter water). After inoculation, the leaves were kept in a high-humidity chamber. After 10 days, the amount of disease control was determined. The percent disease control provided by the test compound was based on the percent disease reduction relative to untreated check leaves. The test compound, the test concentration and the percent control are tabulated in Table II.

TABLE II

| | Preventive Grape Downy Mildew Control | | |
|---|---|---|---|
| Test Compound | Percent Control | | |
| | 40 ppm | 16 ppm | 6.4 ppm |
| Compound A | 100 | 100 | 100 |
| Folpet | 97.7 | 98.8 | 80.1 |
| Captafol | 96.5 | 98.8 | 95.3 |

EXAMPLE 8 — FERMENTATION TEST

An in-vitro test was carried out to determine the influence of 3-(N-chloroacetyl-N-2,6-dimethylphenylamino)-gamma-butyrolactone (Compound A) on yeasts responsible for the alcoholic fermentation of grapes. The test was conducted as follows:

Erlenmeyer flasks (500 cc) were filled with 200 cc of grape juice (density 1.07 gm/cc) extracted from bunches of *Madeleine Angevine* grapes. The test compound was added to the grape juice and the extent of fermentation determined by measuring the cumulative loss of weight due to carbon dioxide escape. For comparison, the test was conducted with an untreated check and a commercial fungicide. The concentration of test compound and the results for the first 8 days of fermentation are tabulated in Table III.

TABLE III

| Product added | Conc. ppm | Fermentation Test Cumulative loss of weight (in grams) due to $CO_2$ escape after | | | | | |
|---|---|---|---|---|---|---|---|
| | | 1 day | 2 days | 3 days | 4 days | 7 days | 8 days |
| Comp. A | 1 | 0.9 | 5.0 | 10.5 | 11.3 | 14.2 | 14.5 |
| | 2 | 0.8 | 5.2 | 10.4 | 11.1 | 13.4 | 13.7 |
| | 4 | 1.0 | 5.2 | 10.4 | 11.1 | 13.1 | 13.3 |
| | 8 | 1.0 | 5.4 | 11.0 | 11.8 | 14.5 | 15.2 |
| Commercial | 1 | 0.4 | 0.5 | 2.8 | 3.6 | 8.9 | 10.1 |
| Fungicide | 2 | 0.2 | 0.4 | 1.3 | 1.8 | 4.7 | 5.6 |
| | 4 | 0.4 | 0.4 | 0.7 | 0.8 | 2.1 | 3.1 |
| | 8 | 0.3 | 0.4 | 0.7 | 0.7 | 1.2 | 1.5 |
| None | — | 0.9 | 5.4 | 11.1 | 11.6 | 14.2 | 14.5 |

EXAMPLE 9 — ERADICANT DOWNY MILDEW CONTROL 3-(N-chloroacetyl-N-2,6-dimethylphenylamino)-gamma-butyrolactone (Compound A) and several commercial fungicides were tested for the eradicant control of downy mildew (*Plasmopara viticola* on grape leaves. The commercial fungicides employed were:

Captafol — cis-N-(1,1,2,2-tetrachloroethylthio)-4-cyclohexene-1,2-dicarboximide
Fentinacetate — triphenyltin acetate
Chlorothalonil — 2,4,5,6-tetrachloroisophthalonitrile
Cupric sulfate Detached leaves of Carignane and Emperor grape plants were used as hosts. The leaves were inoculated with the organism and placed in an evironment chamber and incubated at 18°-22° C and at about 100% relative humidity for 1 to 3 days (1 to 2 days for Emperor leaves, 3 days for Carignane leaves). The leaves were then sprayed with a solution of the test compound in acetone. The sprayed leaves were then maintained at 18°-22° C. and at about 100% relative humidity. Eight to nine days after inoculation, the amount of disease control was determined. The percent disease control provided by a given test compound was based on the percent disease reduction relative to nontreated check leaves. The test compound, the grape leaf variety, the time of treatment with the test compound (days after inoculation) and the results of $ED_{50}$ (ppm of applied spray for 50% control) and $ED_{90}$ (ppm of applied spray for 90% control) are tabulated in Table IV.

TABLE IV

| | Eradicant Grape Downy Mildew Control | | |
|---|---|---|---|
| | Eradication $ED_{50}/Ed_{90}$ | | |
| | Emperor Leaves | | Carignane Leaves |
| Test Compound | 1 day | 2 days | 3 days |
| Compound A | 9.3/58 | 27/99 | 20.7/113 |
| Captafol | 55/145 | 64/168 | 206/670 |
| Fentinacetate | 47/171 | 88/219 | 254/562 |
| Chlorothalonil | 128/293 | 410/1000+ | 313/992 |
| Cupric sulfate* | 118/289 | 204/445 | 380/610 |

*Water used as solvent

EXAMPLE 10 — ERADICANT DOWNY MILDEW CONTROL

A wettable powder formulation of 3-(N-chloroacetyl-N-2,6-dimethylphenylamino)-gamma-butyrolactone in attapulgite clay was tested for the eradicant control of grape downy mildew on grape leaves. Three-month-old single-bud Cabernet Sauvignon cuttings (cultivated in gravel) containing 6 to 10 leaves were used as hosts. The undersides of the leaves were sprayed with a sporangial suspension of *Plasmopara viticola* containing 510,000 conidia per milliliter of water. The inoculated cuttings were placed into a misting chamber. An aqueous suspension containing 62.5 ppm of test compound was sprayed on the cuttings at a rate of approximately 3.5 ml per 100 cm² of leaves at four different dates after the date of inoculation. Ten to 11 days after the inoculation, the amount of disease control was determined. The percent disease control provided by the test compound was based on the percent disease reduction relative to untreated check cuttings. The results are tabulated in Table V.

TABLE V

| Eradicant Grape Downy Mildew Control | | | |
|---|---|---|---|
| Interval between inoculation and fungicide treatment (in days) | Conc. of Fungicide (ppm) | % Leaf Surface Infected | % Disease Control |
| 1 | 0 | 21 | — |
| 1 | 62.5 | 0.51 | 97.6 |
| 2 | 0 | 14.3 | — |
| 2 | 62.5 | 0.55 | 96.2 |
| 3 | 0 | 27.14 | — |
| 3 | 61.5 | 4.15 | 84.7 |
| 5 | 0 | 29.84 | — |
| 5 | 62.5 | 2.5 | 91.6 |

EXAMPLE 11 — RESIDUAL PREVENTIVE GRAPE DOWNY MILDEW CONTROL

A wettable powder formulation of 3-N-chloroacetyl-N-2,6-dimethylphenylamio)-gamma-butyrolactone in attapulgite clay was tested for residual preventive downy mildew control on grape leaves. Three-month-old single-bud Cabernet Sauvignon cuttings (cultivated in gravel), containing 5 to 8 leaves, were used as hosts. The cuttings were sprayed with an aqueous suspension containing 160 ppm of the test compound at a rate of approximately 4 ml/100 cm² of leaves. The cuttings were then placed in a humid chamber at 90 to 95% relative humidity. Three days after fungicide treatment, the undersides of the leaves were sprayed with a sporangial suspension of *Plasmopara viticola*. The inoculated cuttings were put into a misting chamber. Eight to 10 days after the inoculation, the amount of disease control was determined. The percent disease control provided by the test compound was based on the percent disease reduction relative to untreated check cuttings. The results are tabulated in Table VI.

TABLE VI

| Residual Preventive Grape Downy Mildew Control | | | |
|---|---|---|---|
| Interval between inoculation and fungicide treatment (in days) | Conc. of Fungicide (ppm) | % Leaf Surface Infected | % Disease Control |
| 3 | 0 | 12.81 | — |
| 3 | 160 | 0.03 | 99.8 |

EXAMPLE 12 — CONTROL OF FOLIAR DOWNY MILDEW INFECTION BY ROOT ABSORPTION

A 50% wettable powder formulation of 3-(N-chloroacetyl-N-2,6-dimethylphenylamio)-gamma-butyrolactone in attapulgite clay was tested for the control of foliar grape downy mildew infection by root absorption. Three-month-old single-bud Cabernet Sauvignon cuttings (cultivated in gravel), containing 9 to 12 leaves, were used as hosts. The roots of the cuttings were dipped for 6 hours in an aqueous suspension containing 50 ppm of the test compound. The cuttings were then replanted in gravel and put into a misting chamber. At four different times after root treatment, the leaf undersides were sprayed with a sporangial suspension of *Plasmopora viticola*. The inoculated cuttings were placed into the misting chamber to stimulate disease development. Ten to 12 days after inoculation, the amount of disease control was determined. The percent disease control provided by the test compound was based on the percent disease reduction relative to untreated check cuttings. The results are tabulated in Table VII.

TABLE VII

Control of Grape Downy Mildew by Root Absorption

| Interval between root treatment and inoculation (in days) | Conc. of Fungicide (ppm) | % Leaf Surface Infected | % Disease Control |
| --- | --- | --- | --- |
| 1 | 0 | 10.92 | — |
| 1 | 50 | 6.26 | 33.5 |
| 5 | 0 | 17.51 | — |
| 5 | 50 | 0.32 | 98 |
| 9 | 0 | 10.11 | — |
| 9 | 160 | 0.19 | 99 |
| 16 | 0 | 39.35 | — |
| 16 | 160 | 22.43 | 43 |

EXAMPLE 13 — CONTROL OF LETTUCE DOWNY MILDEW

A 50% wettable powder formulation of 3-(N-chloroacetyl-N-2,6-dimethylphenylamino)-gamma-butyrolactone in attapulgite clay was tested for the control of the lettuce downy mildew organism, *Bremia lactucae*.

Lettuce seeds (cultivar Marty) were planted in plastic flats filled with a mixture of ⅔ compost and ⅓ sandy soil. The flats were left in a greenhouse (17°-24° C.) Six days after planting, the lettuce seedlings (cotyledon stage) were sprayed with an aqueous suspension of the test compound at various test concentrations (one flat per concentration level). One day after fungicide application, the seedlings were sprayed with a sporangial suspension containing 140,000 conidia of the organism per milliliter water. The seedlings were placed in a humid chamber (12°-14° C., 12 hours per day of artificial light). Eight days after inoculation, the amount of disease control was determined by counting the number of surviving seedlings per flat. The results for the test compound, two commercial standards and two untreated checks are tabulated in Table VIII.

TABLE VIII

Lettuce Downy Mildew Control

| Fungicide | Rates g active/hl | Total No. Seedlings per flat | % Dead Seedlings | % Control |
| --- | --- | --- | --- | --- |
| Test Compound | 25 | 689 | 5.9 | 75.8 |
| Test Compound | 50 | 780 | 1.1 | 90.6 |
| Test Compound | 100 | 780 | 2.3 | 95.5 |
| Captafol | 160 | 614 | 3.6 | 85.2 |
| Maneb* | 160 | 422 | 14.5 | 40.6 |
| Untreated uncontaminated check | — | 363 | 1.9 | — |
| Untreated contaminated check | — | 427 | 24.4 | — |

*Manganous ethylene bisdithiocarbamate

EXAMPLE 14 — PREVENTIVE AND CURATIVE CONTROL OF CABBAGE DOWNY MILDEW

A 50% wettable powder formulation of 3-N-chloroacetyl-N-2,6-dimethylphenylamino)-gamma-butyrolactone in attapulgite clay was tested for the control of the cabbage downy mildew organism, *Peronospora parasitica* ssp. *brassicae*.

Preventive Control

Cabbage seeds (cultivar Milan hatif d'Aubervilliers) were planted in plastic flats containing a soil mixture of 3 parts compost and 1 part sand. The seeded flats were maintained in a high-humidity greenhouse environment. Seven days after planting, 3 flats of cabbage seedlings were sprayed until runoff with an aqueous suspension of the test compound at various concentrations. Two days after fungicide application, the flats of cabbage seedlings were sprayed with an aqueous suspension of the conidia (about 300,000 per ml) of the organism. Eleven days after inoculation, amount of disease control was determined by counting the number of diseased seedlings at the 1-leaf stage covered with a white mycelium. The results for flats treated with the test compound, a commercial standard and check flats are tabulated in Table IX.

Curative Control

Cabbage seeds (cultivar Milan hatif d'Aubervilliers) were planted in plastic flats containing a soil mixture of 3 parts compost and 1 part sand. The seeded flats were maintained in a high-humidity environment. Nine days after planting, 3 flats of cabbage seedlings were sprayed with an aqueous suspension of the conidia (about 300,000 per ml) of the organism. Four days after inoculation, the flats were sprayed until runoff with an aqueous suspension of the test compound at various concentrations. Seven days after fungicide application, the amount of disease control was determined by counting the number of diseased seedlings at the 1-leaf stage covered with white mycelium. The results for the flats treated with the test compound, a commercial standard and check flats are tabulated in Table IX.

TABLE IX

Control of Cabbage Downy Mildew

Preventive

| Fungicide | Rates a.i. g/hl | Total No. of Seedlings | % Diseased Seedlings | % Control* |
| --- | --- | --- | --- | --- |
| Compound A | 80 | 231 | 1.5 | 98.5 |
| Compound A | 40 | 138 | 2.2 | 97.7 |
| Compound A | 20 | 171 | 1.8 | 98.2 |
| Captafol | 160 | 161 | 59.6 | 38.9 |
| None/inoculated | — | 175 | 97.6 | — |
| None/not inoculated | — | 177 | 1.7 | — |

Curative

| | Rates a.i. | Total No. of | % Diseased | % |

TABLE IX-continued

| Fungicide | g/hl | Seedlings | Seedlings | Control* |
|---|---|---|---|---|
| Compound A | 80 | 155 | 0.6 | 99.4 |
| Compound A | 40 | 203 | 1.0 | 99.0 |
| Compound A | 20 | 165 | 1.8 | 98.2 |
| Captafol | 160 | 148 | 65.5 | 32.9 |
| None/inoculated | — | — | — | — |
| None/not inoculated | — | — | — | — |

*Disease reduction relative to check flat which was not treated with fungicide.

EXAMPLE 15 — FOLIAR TREATMENT OF CUCUMBER DOWNY MILDEW

Compound A was tested by a foliar spray application for the control of the cucumber downy mildew organism *Pseudoperonospora cubensis*.

A 3-week old cucumber plant (cultivar Marketeer) was sprayed with a solution of the test compound in a 1% acetone/99% water suspension containing 40 ppm of a nonionic surfactant. Four leaves were detached from the plant, dried and inoculated by spraying with a spore suspension of the organism. After inoculation, the leaves were kept at 20°–25° C. in a high-humidity chamber. After 6 days, the amount of disease infection was determined. The percent disease control provided by the test compound was based on the percent disease reduction relative to untreated check leaves. The test compound, the test concentration and the percent control are tabulated in Table X.

TABLE X
Foliar Spray Control of Cucumber Downy Mildew

| Test Compound | Conc. (ppm) | % Control |
|---|---|---|
| Compound A | 100 | 100 |
| Compound A | 40 | 88 |
| Compound A | 16 | 63 |
| Maneb | 100 | 98.3 |
| Maneb | 40 | 90 |
| Maneb | 16 | 80 |

EXAMPLE 16 — CONTROL OF SNAPDRAGON CROWN AND ROOT ROT

Compound A was tested to determine its activity against the crown and root rot organism *Phytophthora cryptogea* on snapdragon plants (cultivar *Antirrhinum*). For comparison, Captafol and Mancozeb were included in the test.

Soil Drench

Four pots filled with young plants were transplanted into 13-cm soil infected with the organism. Forty ml of a 100-ppm aqueous solution of the test compound was poured in the pots. The plants were then maintained in a greenhouse for disease development. Five days after treatment, the plants were rated for leaf necrosis and wilt, and crown rot. The percent disease control provided by the test compound was based on disease reduction related to non-treated check plants. The results are tabulated in Table XI.

Folair Spray

Young plants were transplated into 13-cm pots (4) filled with soil infected with the organism. The soil was covered with a plastic covering and the plant foliage was sprayed to runoff with 100 ppm aqueous suspension of the test compound. The plants were then placed in a greenhouse for disease development. Five days after treatment, the plants were rated for leaf necrosis and wilt, and crown rot. The percent disease control provided by the test compound was based on disease reduction related to non-treated check plants. The results are tabulated in Table XI.

TABLE XI
Snapdragon Crown and Root Rot Control

| Compound | % Control Soil Drench | % Control Foliar Spray |
|---|---|---|
| A | 100 | 97 |
| Captafol | 0 | 0 |
| Mancozeb* | 0 | 0 |

*{[1,2-ethanediylbis(carbamodithioato)](2-)} manganese mixture with {[1,2-ethanediylbis(carbamodithioato)](2-)}-0 zinc

EXAMPLE 17 — SYSTEMIC FOLIAR TREATMENT FOR SAFFLOWER CROWN AND ROOT ROT CONTROL

Compound A was tested to determine its systemic activity in foliar applications against the crown and root rot organism *Phytophthora cryptogea*.

Two-week-old safflower seedlings were used as hosts. Pots containing the seedlings were sprayed with an aqueous solution of the test compound at various test concentrations. One day after treatment a spawn of the organism was poured on the soil surface in the pots. The spawn was prepared by cultivating the organism in a mixture of oat flakes, potato dextrose and soil. The inoculated seedlings were then maintained in a greenhouse at 20–25° C. and 15–20° C. night temperature. Three to four weeks after inoculation, the plant roots and crown were rated for disease. The percent disease control provided by the test compound was based on percent disease reduction relative to non-treated check plants. The test concentration and the percent disease control are tabulated in Table XII.

TABLE XII
Safflower Crown and Root Rot Control by Foliar Spray

| Compound | Conc. ppm | % Control |
|---|---|---|
| Compound A | 100 | 100 |
|  | 40 | 97 |
|  | 16 | 92 |
| (2,6-dimethylphenyl-N-(chloroacetyl)-N-(1-methoxycarbonylethyl)) | 100 | 10 |
|  | 40 | 0 |
|  | 16 | 0 |
| Standard** (5-ethoxy-3-trichloromethyl-1,2,4-thiazole) | 100 | 61 |
|  | 40 | 1 |
|  | 16 | 0 |

**U.S. Pat. Nos. 3,260,588 and 3,260,725

EXAMPLE 18 — SYSTEMIC SOIL DRENCH TREATMENT FOR SAFFLOWER CROWN AND ROOT ROT CONTROL

Compound A was tested to determine its systemic activity in soil-drench applications against the safflower crown and root rot organisms, *Phytophthora cryptogea* and *P. parasitica*.

Two-week-old safflower seedlings were used as hosts. Pots containing the seedlings were drenched with an aqueous suspension of the test compound at various test concentrations (four pots per concentration level). One day after treatment a spawn of the organism was poured on the soil surface in the pots. The spawn was prepared by cultivating the organism in a mixture of oat flakes, potato dextrose and soil. The inoculated seedlings were then maintained in a greenhouse at 20–25° C. day and 15–20° C. night temperature. Three to four weeks after inoculation, the plant roots and crown were rated for disease. The percent disease control provided by the test compound was based on percent disease reduction relative to non-treated check plants. The test concentrations and the percent disease control are tabulated in Table XIII.

TABLE XIII

| Safflower Crown and Root Rot Control by Soil Drench | | | |
|---|---|---|---|
| | Conc. | % Control | |
| Compound | ppm | P. Cryptogea | P. Parasitica |
| Compound A | 100* | 100 | 100 |
| | 40 | 97 | 99 |
| | 16 | 92 | 94 |
| Standard** (5-ethoxy-3- | 100 | 78 | 80 |
| trichloromethyl-1,2,4- | 40 | 12 | 21 |
| thiadiazole) | 16 | 0 | 0 |

*100 ppm = 50 micrograms/cm$^2$ = 4.46 lbs.acre
**U.S. Pat. Nos. 3,260,588 and 3,260,725

EXAMPLE 19 — SYSTEMIC SOIL DRENCH TREATMENT FOR TOBACCO CROWN AND ROOT ROT CONTROL

Compound A was tested to determine its systemic activity in soil-drench applications against the crown and root rot organisms *Phytophthora parasitica* and *P. cryptogea*.

Ten-week-old tobacco seedlings (cultivar Glurk) were used as hosts. Pots containing the seedlings were drenched with an aqueous solution of the test compound at various test concentrations (4 pots per concentration level). One day after treatment a spawn of the organism was poured on the soil surface in the pots. The spawn was prepared by cultivating the organism in a mixture of oat flakes, potato dextrose and soil. The inoculated seedlings were then maintained in a greenhouse at 20°–25° C day and 15°–20° C night temperature. Three to four weeks after inoculation, the plant roots and crown were rated for disease. The percent disease control provided by the test compound was based on percent disease reduction relative to non-treated check plants. The test concentration and the percent disease control are tabulated in Table XIV.

TABLE XIV

| Tobacco Crown and Root Rot Control by Soil Drench | | | |
|---|---|---|---|
| | Conc. | % Control | |
| Compound | ppm | P. Cryptogea | P. Parasitica |
| Compound A | 100* | 100 | 100 |
| Compound A | 40 | 99.8 | 99.8 |
| Compound A | 16 | 96 | 96 |
| Standard** (5-ethoxy-3- | 100 | 80 | 52 |
| trichloromethyl-1,2,4- | 40 | 48 | 30 |

TABLE XIV-continued

| Tobacco Crown and Root Rot Control by Soil Drench | | | |
|---|---|---|---|
| | Conc. | % Control | |
| Compound | ppm | P. Cryptogea | P. Parasitica |
| thiadiazole) | 16 | 9 | 0 |

*100 ppm = 50 micrograms/cm$^2$ = 4.46 lbs/acre
**U.S. Pat. No. 3,260,588 and 3,260,725

EXAMPLE 20 – CONTROL OF PHYTOPHTHORA ROT IN SWEET PEPPERS

A 50% wettable powder formulation of 3-N-chloroacetyl-N-2,6-dimethylphenylamino)-gamma-butyrolactone in attapulgite clay was tested for the control of Phytophthora rot in sweet peppers caused by the soil-inhabiting *Phytophthora capsici* organism.

Sweet pepper seedlings (cultivar Doux de Valence) at the 4-leaf stage were planted in pots filled with a sterilized mixed soil of ½ compost and ½ sandy soil. The pots were then inoculated with the organism by spreading a bed of oats grain (contaminated with the *Phytophthora capsici* organism) on the soil surface and covering the bed with a 1-cm depth of sterilized soil. The sweet pepper seedlings were then sprayed to runoff with an aqueous suspension of the test compound at various test concentrations (12 pots per concentration level). The amount of disease control was determined by counting the number of dead plants. The percent disease control provided by the test compound was based on the percent disease reduction relative to untreated check seedlings. The results are tabulated in Table XV.

TABLE XV

| Control of Pepper Phytophthora Rot | | | |
|---|---|---|---|
| Conc. of Fungicide g/hl | % of Alive Seedlings | % Control | % Leaf Surface Damaged |
| 100 | 50 | 25 | 0 |
| 200 | 100 | 100 | 1.3 |
| 400 | 100 | 100 | 1.63 |
| 0 | 33.3 | — | 0 |

What is claimed is:

1. A method for controlling *Phytophthora* crown or root rot diseases which comprises applying to the growth medium of plants or plant hosts of *Phytophthora* fungi a fungicidally effective amount of a compound of the formula.

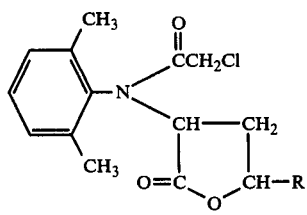

wherein R is hydrogen or methyl.

2. A method in accordance with claim 1 wherein the plants are tobacco, snapdragon, safflower or pepper.

3. A method in accordance with claim 1 wherein R is hydrogen.

* * * * *

UNITED STATES PATENT AND TRADEMARK OFFICE
CERTIFICATE OF CORRECTION

PATENT NO. : 4,141,989

DATED : February 27, 1979

INVENTOR(S) : David C. K. Chan

It is certified that error appears in the above-identified patent and that said Letters Patent are hereby corrected as shown below:

Col. 1, line 19, "Jan. 27" should read --Jan. 26--.

Col. 5, line 41, "formulations" should read --formulation--.

Col. 6, line 45 "ater" should read --after--. Col. 7,

Table I (cont'd), "$Ch_2Cl$" should read --$CH_2Cl$--.

Col. 7, line ~40, omitted, should read

--**N-(1-methoxycarbonylethyl-N-alpha-chloroacetyl-2,6-dimethylaniline (U.K. Patent 1,445,387)
***cis-N-(1,1,2,2-tetrachloroethylthio)-4-cyclohexene-1,2-dicarboximide--.

Col. 9, line 47 "$Ed_{90}$" should read --$ED_{90}$--.

Col. 10, line 42, "...amio" should read --...amino--.

Col. 11, line 5, "...amio" should read --...amino--.

Col. 12, line 15, "3-N-" should read --3-(N- --.

Col. 13, line 58, "Folair" should read --Foliar--.

Col. 14, line 11, "0-zinc" should read --zinc--.

UNITED STATES PATENT AND TRADEMARK OFFICE
CERTIFICATE OF CORRECTION

PATENT NO. : 4,141,989                                        Page 2 of 2

DATED      : February 27, 1979

INVENTOR(S) : David C. K. Chan

It is certified that error appears in the above-identified patent and that said Letters Patent are hereby corrected as shown below:

Col. 14, line 28, "and" should read --day and--.

Col. 14, line 45, "  C  " should read --   C --.
                            -N                           -N C                            C
                             "                            '
                             C                            C Col. 14, line 49, "thiazole" should read --thiadiazole--.

Signed and Sealed this

Sixth     Day of    November 1979

[SEAL]

Attest:

RUTH C. MASON
*Attesting Officer*

LUTRELLE F. PARKER
*Acting Commissioner of Patents and Trademarks*